United States Patent
Jackson et al.

(10) Patent No.: US 8,753,496 B2
(45) Date of Patent: Jun. 17, 2014

(54) METHOD FOR MONITORED SEPARATION AND COLLECTION OF BIOLOGICAL MATERIALS

(75) Inventors: George William Jackson, Houston, TX (US); Richard Coale Willson, Houston, TX (US); George Edward Fox, Houston, TX (US)

(73) Assignee: Board of Regents, University of Houston, Houston, TX (US)

( * ) Notice: Subject to any disclaimer, the term of this patent is extended or adjusted under 35 U.S.C. 154(b) by 695 days.

(21) Appl. No.: 12/928,650

(22) Filed: Dec. 16, 2010

(65) Prior Publication Data

US 2011/0100818 A1      May 5, 2011

Related U.S. Application Data

(63) Continuation of application No. 11/091,605, filed on Mar. 28, 2005, now Pat. No. 7,875,162.

(60) Provisional application No. 60/556,784, filed on Mar. 26, 2004.

(51) Int. Cl.
  *G01N 27/447* (2006.01)
  *B01D 15/10* (2006.01)
  *B01D 15/24* (2006.01)
  *B01D 57/02* (2006.01)
  *C12N 15/10* (2006.01)

(52) U.S. Cl.
  CPC ...... *C12N 15/1003* (2013.01); *G01N 27/44721* (2013.01); *B01D 57/02* (2013.01)
  USPC ............................ 204/456; 204/450; 210/656

(58) Field of Classification Search
  USPC ............. 210/656; 422/70; 204/600, 450, 456, 204/606
  See application file for complete search history.

(56) References Cited

U.S. PATENT DOCUMENTS

| | | |
|---|---|---|
| 3,791,950 A | 2/1974 | Allington |
| 3,879,280 A | 4/1975 | Peterson et al. |

(Continued)

FOREIGN PATENT DOCUMENTS

JP       63-81256 A   *   4/1988   ............. G01N 27/26

OTHER PUBLICATIONS

Thomson Reuters English language abstract for Fujii H JP 63081256 A, patent published Apr. 12, 1988.*

(Continued)

*Primary Examiner* — Alex Noguerola
(74) *Attorney, Agent, or Firm* — Thompson & Knight, LLP; Jennifer S. Sickler

(57) ABSTRACT

A device for separating and purifying useful quantities of particles comprises: (a) an anolyte reservoir connected to an anode, the anolyte reservoir containing an electrophoresis buffer; (b) a catholyte reservoir connected to a cathode, the catholyte reservoir also containing the electrophoresis buffer; (c) a power supply connected to the anode and to the cathode; (d) a column having a first end inserted into the anolyte reservoir, a second end inserted into the catholyte reservoir, and containing a separation medium; (e) a light source; (f) a first optical fiber having a first fiber end inserted into the separation medium, and having a second fiber end connected to the light source; (g) a photo detector; (h) a second optical fiber having a third fiber end inserted into the separation medium, and having a fourth fiber end connected to the photo detector; and (i) an ion-exchange membrane in the anolyte reservoir.

19 Claims, 3 Drawing Sheets

(56) References Cited

U.S. PATENT DOCUMENTS

| | | |
|---|---|---|
| 4,323,439 A | 4/1982 | O'Farrell |
| 4,421,735 A | 12/1983 | Haber |
| 4,479,861 A * | 10/1984 | Hediger ............ 204/615 |
| 4,521,512 A * | 6/1985 | Silman ............ 435/35 |
| 4,877,510 A | 10/1989 | Chen |
| 4,975,583 A | 12/1990 | Spowart |
| 5,064,519 A * | 11/1991 | Tice et al. ............ 204/466 |
| 5,151,165 A | 9/1992 | Huynh |
| 5,207,880 A * | 5/1993 | Middendorf et al. ......... 204/461 |
| 5,284,559 A | 2/1994 | Lim et al. |
| 5,410,412 A | 4/1995 | Gombocz et al. |
| 5,443,704 A | 8/1995 | Kirkpatrick et al. |
| 5,641,893 A | 6/1997 | Penn |
| 6,004,443 A | 12/1999 | Rhodes et al. |
| 6,793,790 B1 | 9/2004 | Olivares et al. |
| 7,070,987 B2 | 7/2006 | Cunningham et al. |

OTHER PUBLICATIONS

Holmes, Diana L. et al, "Estimation of polyacrylamide gel pore size from Ferguson plots of linear DNA fragments II. Comparison of gels with different crosslinker concentrations, added agarose and added linear polyacrylamide." Electrophoresis, 12, 612-619. 1991.

Jones, K. "A review of biotechnology and large scale affinity chromatography." Chromatographia vol. 32, No. 9/10, Nov. 1991.

* cited by examiner

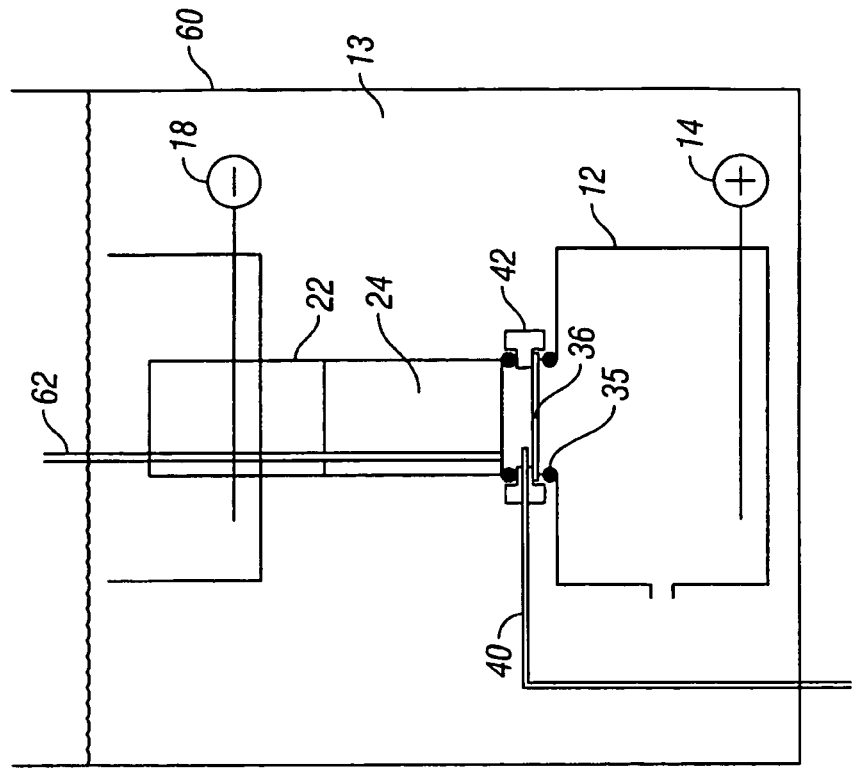
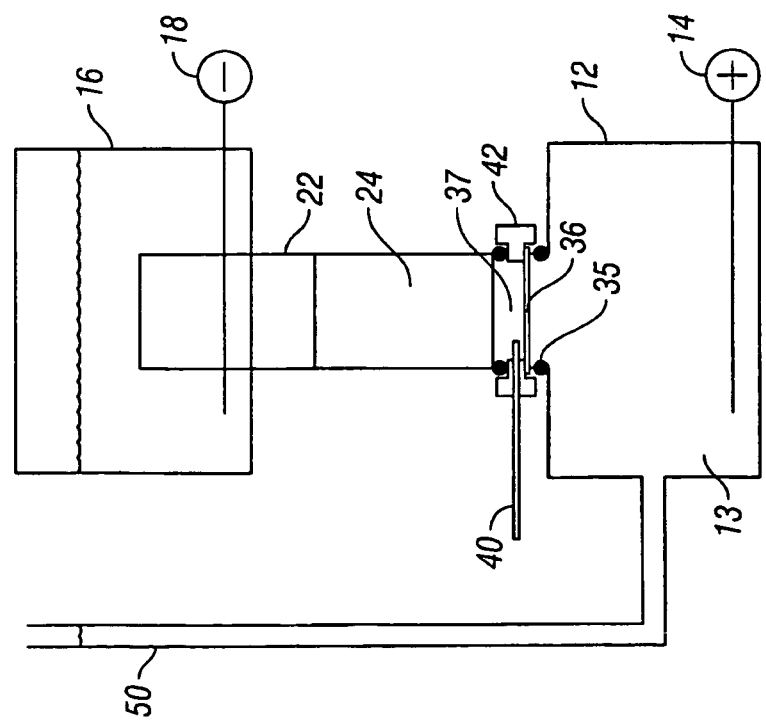
Fig. 2B
Fig. 2A

METHOD FOR MONITORED SEPARATION AND COLLECTION OF BIOLOGICAL MATERIALS

CROSS-REFERENCE TO RELATED APPLICATIONS

This application claims the benefit of U.S. Provisional Patent Application No. 60/556,784, filed Mar. 26, 2004; and it is a continuation of U.S. patent application Ser. No. 11/091,605, filed on Mar. 28, 2005 now U.S. Pat. No. 7,875,162.

REFERENCE TO A "SEQUENTIAL LISTING", A TABLE, OR A COMPUTER PROGRAM LISTING APPENDIX SUBMITTED ON A COMPACT DISC

Not Applicable.

STATEMENT REGARDING FEDERALLY SPONSORED RESEARCH OR DEVELOPMENT

The U.S. Government has a paid-up license in this invention, and the right in limited circumstances to require the patent owner to license others on reasonable terms as provided for by the terms of Grant No. G005182 awarded by the NASA/NSBRI (National Space Bio-Medical Research Institute).

BACKGROUND OF THE INVENTION

The present invention relates to the general fields of biotechnology, molecular biology, clinical diagnosis, or any field requiring the preparation, purification, and isolation of biological molecules, nucleic acids, proteins, and particles, referred to generally in this patent as particles. The invention particularly relates to methods for purifying nucleic acids and proteins by electrophoresis, preparative electrophoresis, electrochromatography, and electro-elution.

DESCRIPTION OF THE RELATED ART

Following isolation of a nucleic acid mixture from a biological sample, size fractionation is routinely the first step of subsequent procedures. For many applications, conventional agarose or polyacrylamide gel electrophoresis followed by gel extraction techniques yields sufficient quantity of the desired nucleic acid molecule. This is especially true when PCR amplification will be used to increase the amount of obtained material. For some applications, however, sufficient quantity of material is not easily obtained directly from small, analytical slab gels, or gel extraction techniques do not reproducibly provide sufficient quantity of sample. Furthermore, gel extraction generally requires considerable time and reagents. Gel extraction procedures also increase the opportunity for sample degradation to occur, and the reagents used may be incompatible with downstream analysis or subsequent manipulations.

For larger preparations, liquid (pressure driven) chromatographic methods can be employed. However, liquid chromatography (LC) columns generally provide less separation efficiency (fewer number of theoretical plates) than electrophoretic gels. Different mixtures generally require development of specifically tailored protocols and chromatographic media when designing an LC separation. Finally, LC equipment is generally more costly than electrophoresis devices.

The following U.S. patents disclose existing electrophoresis devices. These patents are incorporated herein by this reference:

Rhodes, et al., U.S. Pat. No. 6,004,443, "Chromatography-format fluid electrophoresis", Dec. 21, 1999;
Lim, et al., U.S. Pat. No. 5,284,559, "Preparative electrophoresis device and method", Feb. 8, 1994;
Chen, U.S. Pat. No. 4,877,510, "Apparatus for preparative gel electrophoresis", Oct. 31, 1989.

Most preparative electrophoresis techniques require additional reagents and time consuming extraction steps to isolate the biological molecule from the electrophoretic gel following a slab-gel separation. Prior "column-like" preparative electrophoresis systems typically employ a complicated arrangement of pumps, sample collection equipment, cooling equipment, and detectors. What is needed is a simplified monitored electrophoretic separation device having a minimal elution reservoir volume for efficient precipitation, while still controlling the pH.

SUMMARY OF THE INVENTION

A device for separating and purifying useful quantities of particles comprises: (a) an anolyte reservoir connected to an anode, the anolyte reservoir containing an electrophoresis buffer; (b) a catholyte reservoir connected to a cathode, the catholyte reservoir also containing the electrophoresis buffer; (c) a power supply connected to the anode and to the cathode; (d) a column having a first end inserted into the anolyte reservoir, a second end inserted into the catholyte reservoir, and containing a separation medium; (e) a light source; (f) a first optical fiber having a first fiber end inserted into the separation medium, and having a second fiber end connected to the light source; (g) a photo detector; (h) a second optical fiber having a third fiber end inserted into the separation medium, and having a fourth fiber end connected to the photo detector; and (i) a macromolecule-impermeability membrane in the anolyte reservoir, that creates a smaller collection reservoir within the anolyte reservoir.

BRIEF DESCRIPTION OF THE DRAWINGS

FIG. 2A is a depiction of an alternate embodiment of the invention, with a shortened gel column, and a standpipe.

FIG. 2B is a depiction of another alternate embodiment of the invention, with a shortened gel column, wherein the entire device is submerged in a container.

DETAILED DESCRIPTION OF THE PREFERRED EMBODIMENT

Figure 1:
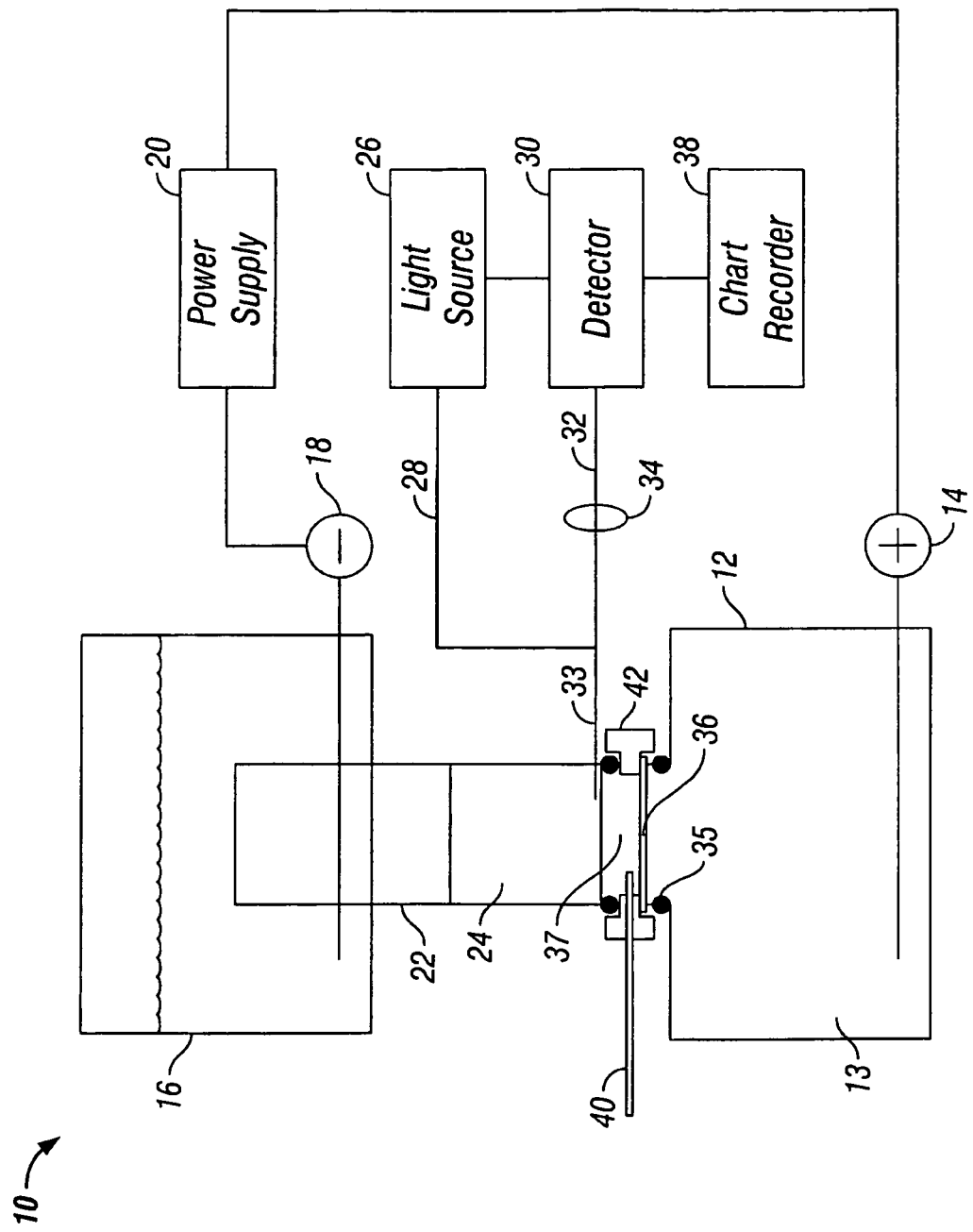
FIG. 1 is a depiction of a preparative electrophoresis column using optical fiber to monitor nucleic acids.

In FIG. 1, a monitored separation device 10 includes an anolyte reservoir 12 connected to an anode 14. The anolyte reservoir 12 contains an electrophoresis buffer 13, which can be any electrophoresis buffer suitable for the separation. Some of the buffers known to those skilled in the art include Tris-Acetate-EDTA (TAE), Tris-Borate-EDTA (TBE), Sodium Borate, denaturing buffers, "MOPS", etc. The monitored separation device 10 is compatible with any buffering system. The monitored separation device 10 also includes a catholyte reservoir 16 connected to a cathode 18. The catholyte reservoir 16 also contains the electrophoresis buffer 13. A power supply 20 connects to the anode 14 and to the cathode 18. A column 22 connects the anolyte reservoir 12 to the catholyte reservoir 16. In an alternate embodiment, the column 22 may be a multi-bore or multi-lumen tubing so that a nucleic acid sizing ladder may also be loaded onto the column 22 and eluted into a divided collection reservoir. Direct comparison to the sizing ladder concentrations or to previous runs enables the monitored separation device 10 to be quantitative. Furthermore, direct generation of a chromatogram enables the monitored separation device 10 to quantify particular nucleic acid bands (peaks) without the use of gel imaging devices, transilluminators, etc. Data collection by a computer allows programming for automated fraction collection and data archiving.

The column 22 contains a separation medium 24. The separation medium 24 is an electrophoretic gel matrix. The anolyte reservoir 12 and the catholyte reservoir 16 are separated such that a hydrostatic pressure difference develops across the separation medium 24 without the addition of the standpipe shown in the left of FIG. 2.

The separation medium 24 is prepared as follows. Agarose gels are cast in the conventional manner by pouring the agarose melt directly into the open column 22 standing on parafilm. Once the gel is cured, the column 22 is removed from the parafilm and placed into the monitored separation device 10. Any type of chromatographic media may be used with this invention. The polymerization of polyacrylamide is quenched in the presence of oxygen. However, polyacrylamide gels can be simply cast in the open column 22 by purging the headspace above the column 22 with an inert gas such as nitrogen or helium until the polymerization is complete.

The monitored separation device 10 is also compatible for use with any other type of chromatographic affinity, affinity-ligand, particle bed, monolithic matrix, hydrophobic interaction, or anion exchange media in which the driving force through the column is electrically induced, although other driving forces are compatible. Furthermore, different concentrations of gel may be poured in the same column 22 to create a "stacking" gel.

Any standard methods for minimizing thermal gradients within the gel may be employed without effect to the fiber optic detection method. The gel may be cooled by insertion of an inner heat exchanging tube, peltier device, etc.

A fiber optic light source or laser 26 connects to an optical fiber 28. The light source 26 functions as a fluorescence excitation source.

A photo detector 30 detects light from an optical long pass filter 34 which filters light from an optical fiber 32. Optical fibers 28 and 32 join together into a bifurcated optical fiber 33, which inserts into the separation medium 24. In an alternate embodiment, the bifurcated optical fiber 33 is not inserted into, but rather is merely immediately juxtaposed to, the separation medium 24. In still another alternate embodiment, the photodetector is directly integrated in the column 22 without a fiber connection. The photo detector 30 is a sensitive fluorescence detector (a PMT-based luminometer) which may be operated in "lock-in" amplification mode at a modulation or "chopping" frequency greater than the 60 Hz of the lights (fluorescent and/or incandescent) typically found in a laboratory. Typical carrier or modulation frequencies for such applications range from 1 kHz to 100 kHz, but any frequency may be chosen. "Chopping" of the fluorescence excitation source 26 on a carrier frequency allows the modulated fluorescence to be detected by very sensitive lock-in-amplification. This detection mode enables the entire device to be used under the ambient light conditions of the laboratory. High quality (high "Q") bandpass circuits for detection of modulated light signals are well known and commonly found in television remote controls, for example. Alternatively, true lock-in amplification can be achieved by modulation-demodulation integrated circuitry, such as Model No. AD630 manufactured by Analog Devices.

An o-ring seal 35 and an ion-exchange membrane 36 in the anolyte reservoir 12 separate the separation medium 24 from the electrophoresis buffer 13 in the anolyte reservoir 12, thus forming a smaller collection reservoir 37. The ion-exchange membrane 36 is a Naflon® 112 membrane, which is a perfluorinated cation exchange membrane.

Nafion® is a copolymer of tetrafluoroethylene and perfluoro-[2(fluorosulfonylethoxy)-vinyl]ether, with the general chemical constitution in the protonated form given as [—(CF2CF2)n-(CF2CF(OCF2CF(CF3)OCF2CF2SO3H))—]x.

The high negative charge of the membrane 36 prevents physisorption of nucleic acids except perhaps by weak cation bridging. Salt and pH conditions in the smaller collection reservoir 37 can be optimized to control such interactions. The chemical inertness of the membrane 36 (derivatized Teflon™) and high ionic conductivity are also attractive features. The membrane 36 can be just about anything that retains, or at least retains a fraction of the molecular weight items that the operator wishes to keep within the collection reservoir, while still allowing electrophoresis to proceed. Nafion® is used in the preferred embodiment because it is highly negatively charged, and thus DNA and RNA do not want to cross. However, the membrane 36 can be any macromolecule-impermeability membrane.

Electrophoresis proceeds in the usual manner with a minimized collection volume at the tip of the column. Previous descriptions of similar devices simply show a minimized anode reservoir or require that a small collection volume be continuously pumped past the end of the electrophoretic column. Such a simple minimization of the anode reservoir does not account for rapid accumulation of protons (lowering pH) at the anode, loss of buffer as evolved gas, or problematic bubble formation that can disturb the local electric field in small volumes or interrupt electrophoresis entirely by breaking the ionic circuit. The smaller collection reservoir 37 allows for passive pH control by a larger, more conventional buffer volume, thereby permitting the smaller collection reservoir 37 to remain at a pH that will not hydrolyze the nucleic acid, proteins, or particles of interest, or disturb electrophoretic separation.

In an alternate embodiment, the column 22 and the smaller collection reservoir 37 may be annular, or a thin flat slab, such that the separation medium 24 has a thin dimension. Such designs are well known to those skilled in the art. Novel selection of electrophoresis buffers can further improve heat management.

A chart recorder 38 connects to the photo detector 30, for displaying the resulting electropherogram. In an alternate embodiment, the chart recorder 38 can be a computer. A syringe tubing 40 inserts into the smaller collection reservoir 37. The syringe tubing 40 inserted through a collar 42 is used to collect fractions. The tubing 40 can pass through the collar 42 and form a seal by any standard means, i.e. glue, ferrule, luer-lock fitting, etc. Alternatively (similar to the capillary bubble-vent in FIG. 2B), the syringe tubing may be affixed to the inside of the column, such that it passes through the separation medium 24. All that is required is that fluidic access to the collection volume 37 is provided. In the preferred embodiment that fluidic access should not greatly increase the total collection volume.

Referring now to FIG. 2A, an alternate embodiment of the monitored separation device 10 requires less total electrophoresis buffer 13. The anolyte reservoir 12 and the catholyte reservoir 16 are separated by a smaller distance than as shown in FIG. 1. Therefore, the addition of a standpipe 50 creates the necessary hydrostatic pressure difference across the separation medium 24.

Referring now to FIG. 2B, a still further alternate embodiment of the monitored separation device 10 is shown. A container 60 filled with the same electrophoresis buffer 13 houses all of the components of the monitored separation device 10 shown in FIG. 2A, except that the standpipe 50 is not used. A capillary bubble vent 62 extends from the smaller collection reservoir 37 above the level of the electrophoresis buffer 13. This capillary bubble vent 62 may also be employed in the configuration shown in FIG. 2A. The advantage of the embodiment shown in FIG. 2B is that the large buffer reservoir 13 formed by 60 allows anolyte and catholyte buffers to be recombined to neutralize pH gradients if desired. Such a reservoir may also be conveniently mixed or temperature controlled. Finally, this embodiment may allow the entire assembly, less the container 60, to be "dropped-in" to existing reservoirs already possessed by the end-user.

In FIGS. 2A and 2B optical monitoring may still be achieved by inserting the bifurcated optical fiber 33 into, or closely opposed to, the separation medium 24.

Other Alternate Embodiments of the Monitored Separation Device 10

The geometry of the device, creation of one or more membrane compartments convenient for sample collection, and detection mechanism are compatible with a number of other approaches to biological separation, detection, and collection of various items, including particles, molecules, nucleic acids, but referred to generally in this patent as "particles". The fluorescent dye may undergo a fluorescence enhancement upon interaction with the biological molecule. The optical fiber may be positioned immediately at the end of the column or slab gel such that the detected nucleic acid species is expected to elute from the column soon thereafter. A mixture of biological molecules (especially nucleic acids) may be premixed with a fluorescent dye that binds to the molecules in the mixture prior to loading on the gel. The fluorescent dye bound to the biological molecule does not prohibitively retard migration through the gel under the electric field, or this retardation may be used advantageously as a separation mechanism. The fluorescent dye or reporting molecule or particle that interacts with the biological molecule may be immobilized on the chromatographic gel matrix. This reporting molecule or particle may be localized or chemically immobilized in the gel only at the detection region or throughout the separation matrix. The fluorescent dye, reporting molecule, or particle may be immobilized on the optical fiber, multiple fibers, or directly on a detector, inserted into the gel matrix. The reporter can be a fluorescent molecular beacon, or hairpin probe, which binds nucleic acid, or a molecular aptamer beacon which binds a protein target Such a reporter can be likewise immobilized either in the separation matrix or directly on the optical fiber or detector such that only a specific sequence of nucleic acid or specific protein target results in a fluorescence enhancement, polarization change, or optical or radioactive signal in general. The reporting molecule may also be a peptide nucleic acid for improved binding kinetics. The reporter may also be a fluorescently labeled nucleic-acid-binding-protein immobilized on the gel matrix. This reporter can be quenched in the presence of molecular target or a conformational change may lead to fluorescence enhancement upon binding to the target.

The radiation source for fluorescence excitation can be a broad, white light source, a light-emitting-diode (LED) or diode laser. The light source can be turned ON and OFF, or "chopped" at a convenient carrier frequency such that the slowly modulated fluorescence intensity due to presence or absence of the molecule, cell, organelle, particle, etc. is detected only at the carrier frequency such that other, ambient light signals are ignored. This would be facilitated by a number of demodulation schemes known to those skilled in the art of signal processing. The detector may be preceded by a high quality (high Q) bandpass filter allowing only the carrier frequency to the detector. A phase-locked-loop (PLL), modulation-demodulation (modem), or similar "lock-in" amplification scheme known to those skilled in the art can be used to detect the fluorescence or other optical signal and reject the ambient light signal. The light source can be chopped at a carrier frequency with a shutter wheel or similar device. The optical detector could also measures polarization, polarization changes, anisotropy, or light scattering. The detector may also measure fluorescence lifetime. The reporter molecule may exhibit an infrared (IR) absorbance or emission.

A number of chromatographic matrices are compatible with the invention. The gel may be polyacrylamide "stacking" gel. Polyacrylamide is conveniently cast in the container described in the invention by purging oxygen with an inert gas above the headspace of the gel during casting. The gel may be of a gradient in polymer, pH, salt, or reagent concentration. The gel or separation media may be an affinity or ligand-modified gel for the analyte mixture.

A number of physical configurations of the device are compatible with the key elements of the invention. The extraction of the sample may be performed at a location other than the end of the column. The entire apparatus or any buffer reservoir or the column may be cooled. The temperature of the column or reservoirs may be controlled and programmable. Cooling or heating may be accomplished by passive design of the geometry or active control through the use of peltier (thermoelectric) devices, fluids for heat exchange, or any other methods commonly employed in conventional electrophoresis apparatuses. The electrophoresis column may be branched so that by controlling the potentials of different reservoirs, the separated bands may be diverted to two or more different reservoirs. As mentioned previously, in the preferred embodiment, any collection reservoir (anode reservoir for nucleic acids), whether one or many is likely to be of a minimized volume for efficient sample precipitation or subsequent manipulation after collection. The collection reservoir (anode or cathode) or gel-loading compartment may be separated from an adjacent, pH-controlling reservoir by an ion-exchange membrane. The pH of the controlling reservoir may be actively controlled or allowed to change over time due to electrolytic reactions in the case of electrophoresis. The anode, cathode, and any ancillary reservoirs may be vented in a convenient manner to allow electrode gases to escape easily. The entire apparatus may be laid horizontally such the buffer reservoirs on each end of the column are hydrostatic. Plugs and vents in the electrode reservoirs are selectable such that the entire apparatus may be positioned vertically or horizontally while still releasing evolved gases. The column and/or buffer reservoirs can be constructed of quartz, acrylic, or other optically transparent materials in the wavelengths of interest such that the separation may be simultaneously or optionally monitored by a UV lamp or transilluminator. In this case, monitoring by optical fiber or integrated detector would be unnecessary or an optional or "switchable" feature. The separation could be monitored by another imaging system such as a commercially available gel documentation system or transilluminator or by the naked eye (properly protected), however, all the other benefits of the invention would be maintained, for example the advantageous placement of ion-exchange or permselective membranes that are compatible with the separation mechanism and create a convenient sample collection volume. The collection reservoir may be filled with a number of possible adsorbent materials which could serve to either further minimize the collection volume or bind specifically to a separated molecule of interest, or to report its presence, or to provide all of these benefits.

The device and innovations described herein are compatible with "separation and reaction" or treatments with reagents or conditions that provide a "second dimension" of separation such as that known as 2D isoelectric focusing followed by SDS PAGE, for example. Denaturants could be "waiting" in a first collection compartment and encountered by the separated molecules, whole cells, organelles, viral particles, beads, or nanoparticles, etc. and a second separation would take place by duplicating the separation, detection, and collection assembly described here. An immobilized enzyme located at a specific region of the separation media providing for an enzymatic reaction in the separation media can be employed. Such a reaction or treatment could also take place in the volume created by the permselective or ion-exchange membrane, or such reagents could be immobilized on the membrane or the membrane itself could act as a catalyst. Those skilled in the art of membrane-electrode-assemblies (MEAS) or immobilizing enzymes and other catalysts in biosensors, fuel-cells, and other redox devices will be familiar with the concept. Following chemical transformation by exposure to such a surface or volume, a second separation could take place by placement of more chromatographic media. The transformation may also have reporting or detection elements or chemistries. The enzymatic reaction region could involve immobilized endoribonuclease acting on a sample mixture of ribonucleic acid (RNA). The enzymatic reaction region could also feasibly contain an immobilized DNA restriction enzyme acting on a sample mixture is of DNA. Such a reaction and preparative device would be useful for generating purified, linearized DNA fragments for cloning. The enzymatic reaction region could contain an immobilized catalytic RNA (ribozyme) or DNA (deoxyribozyme) designed to catalyze a desired reaction prior to further separation.

The exact placement of optical fiber, integrated semiconductor detector, or other detectors or connections to a detector may vary depending on the application and configuration of the apparatus. The optical fiber assembly may be a fiber optic light ring surrounding or immersed in the gel matrix. The optical fiber assembly can be bifurcated for connection to the gel, light source, and detector, or a split bundle. The column is constructed of multi-lumen or multi-bore tubing such that other samples may be loaded and electrophoresed simultaneously in separate "channels" or "lanes". The collection reservoir is divided into multiple chambers to correspond with the number of lanes in the column. In such a configuration, separate optical fibers monitor each channel or lane, and a sizing or reference "ladder" is loaded in one of the lanes for size-reference purposes and/or quantitation. As known to those skilled in the art, the reference ladder would contain known concentrations of molecules in the mixture such that peak heights and areas in the electropherogram may be used to quantify the nucleic acid amounts in the unknown lanes. More than one fluorophore of differing excitation or emission wavelengths which bind specifically to different classes of biological macromolecule could be monitored simultaneously, especially in the preferred embodiment in which the optical fiber could be connected to a spectrophotometer if desired. In most visible, IR, and even UV wavelengths, the entire column can be monitored by a CCD camera, photodiode array, CMOS detector or similar semiconductor device. As mentioned previously, the entire column or portion of the column may be monitored by a photodiode or avalanche photodiode array or linear arrangement of multiple photodiodes or avalanche devices. Furthermore, the chromatographic matrix may be a detection or photoactive material that undergoes an optical property change upon interaction with the specie or a single molecular species being separated in the mixture. The collection volume could be filled with such a "switchable" optically active material. Aqueous solutions and gels or colloidal suspension of materials such as poly(N-isopropylacrylamide) (PNIPAM) conjugated to detection molecules (nucleic acid oligonucleotides, for example) have been shown to undergo phase-changes, precipitation, or changes in optical properties upon binding to their target molecules. Optical fiber monitoring, or integrated photodetection may be replaced by an off-column absorbance, fluorescence, or other detector, but the minimized collection volume may still be created by the perm-selective or ion-exchange membrane. The chromatographic matrix could also be a micro or nanoporous monolith or particle bed. Multiple minimized collection volumes could naturally be created by segmented membrane compartments along the length of the column. If an electric field is used as a driving force (a simplified description of the driving forces involved in electrophoresis) the form of the applied voltage could be any of those known to those skilled in the art. AC or pulsed-fields, or pulsed field gradient electrophoresis are compatible with the device. Particles with and without a chromatographic matrix can be separated in an AC, DC, or DC field superimposed with an AC field in a phenomenon sometimes referred to as dielectrophoresis. The column could also be run in a counteracting chromatographic electrophoresis mode or isoelectric focusing mode. Finally, the column could be run in a continuous mode versus batch loading for all of the processes described here and/or a separation matrix could be used multiple times.

Figure 3:
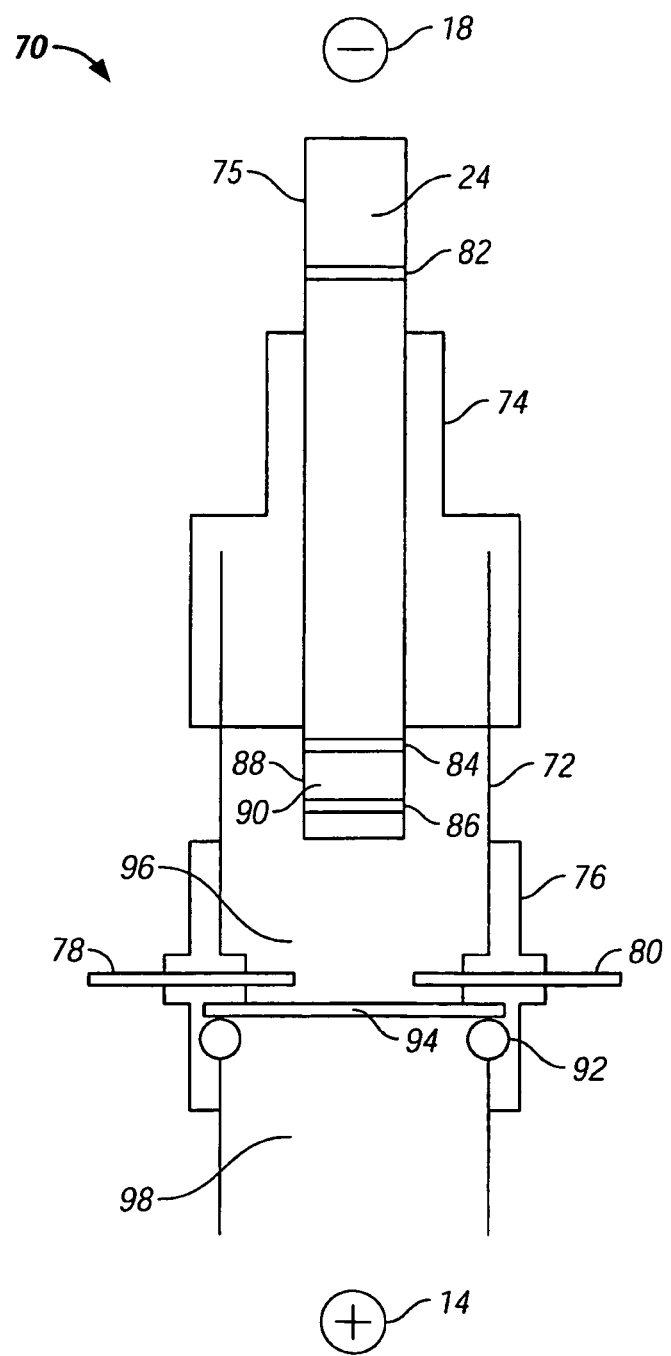
FIG. 3 is a depiction of a preparative electrophoresis column without using an optical fiber to monitor nucleic acids.

Referring now to FIG. 3, an alternate embodiment of the monitored separation device 10 is a monitored separation device 70 which does not use fiber optics to monitor fluorescence. The monitored separation device 70 includes a quartz tube 72 which serves as a viewing window. Connected to the top end of the quartz tube 72 is a reducing adaptor 74. The separation medium 24 is inside a second, smaller quartz tube 75 which is inside the reducing adaptor 74, and protrudes above the level of the reducing adaptor 74. Above the smaller quartz tube 75 is the cathode 18. Below the reducing adaptor 74 is a compression fitting 76 which fits around the quartz tube 72. Inserted through the compression fitting 76, and through the quartz tube 72, is a vent tube 78 and a syringe tube 80. The vent tube 78 may not be necessary depending on the order of assembly, orientation, or whether the device is assembled while submersed. The purpose of the vent tube 78 is to release any trapped bubbles which may affect the separation. Below the bottom end of the quartz tube 72 is the anode 14. The separation medium 24 contains several fluorescent nucleic acid bands 82, 84, and 86 for illustrative purposes. These bands represent schematically how their position might appear while the device is in use. The separation medium 24 fills the smaller quartz tube 75. Just below the level of the vent tube 78 and the syringe tube 80 is an o-ring seal 92 and an ion-exchange membrane 94. Above the ion-exchange membrane 94 is an electrophoresis buffer 96, and below the ion-exchange membrane 94 is another electrophoresis buffer 98. Just as the electrophoresis buffer 13 in FIG. 1 may be any buffer convenient for the particular separation, electrophoresis buffers 96 and 98 may be any buffer solution compatible with the separation, and may the same or different compositions depending on the choice of the user. For illustrative purposes, if nucleic acid band 86 elutes from the gel first and the operator desires to collect this fraction, the electrophoresis buffer 96 will be collected as a sample. A "fresh" electrophoresis buffer 96 will then be introduced through the syringe tube 80. With the electrophoresis buffer 96 replenished, ionic conductivity is restored and electrophoresis will continue. Example bands 82 and 84 can be similarly collected, either as separate fractions or allowed to mix, as they elute off the separation medium 24.

The entire monitored separation device 70 is immersed in the electrophoresis buffer 98, and is compatible with either vertical or horizontal operation. Whether vertical or horizontal, in the preferred embodiment, the container for the electrophoresis buffer 98 will be UV transparent or transparent to the excitation wavelength of the nucleic acid label. If horizontal, the monitored separation device 70 may be excited by a conventional UV transilluminator, and monitored either periodically by eye (with appropriate protection) or by standard gel documentation devices.

In the monitored separation device 70, monitoring of the progress of the nucleic acid or protein-fluorophore complex is accomplished by a UV light source or transilluminator. Using a glass viewing window or glass tube within a tube such a device is easy to fabricate. The monitored separation device 70 uses injection molded parts made of UV transparent plastics, or fluorophores in the visible range. Thus, the monitored separation device 70 can be used with the existing electrophoresis gel boxes already found in molecular biology laboratories.

In another alternate embodiment, UV absorbance measurements can be made with the bifurcated optical fiber 33. As unlabelled nucleic acid or protein migrates past the bifurcated optical fiber 33, less UV back-reflection is measured by the bifurcated optical fiber 33. Such an arrangement eliminates the need for a co-migrating fluorophore.

Both the optical fiber and membrane are employed, however this invention also includes either improvement used alone or in combination. Furthermore, while the preferred embodiment utilizes an electric field as the driving force for molecule, whole cell, or'particle separation (electrophoresis), the on-column optical fiber monitoring and use of one or more permselective membranes for advantageous creation of compartments is compatible with any other conceivable driving force such as a magnetic field (magnetophoresis) or pressure driven flow (pressure driven liquid chromatography, osmotic pressure gradients, density gradient centrifugation, etc). The employed electric, magnetic, thermal, concentration, density gradient, or any other suitable driving force may also be employed in a radial direction through the separation media.

Any fluorophore that binds to the nucleic acid or protein and co-migrates under electrophoresis can be used in the preferred embodiment. It is also possible to operate the optical fiber in a UV-absorbance mode, either using two opposing fibers inserted in the gel or by measuring the amount of UV back-reflectance. Polarization detection is also achievable using optical fibers. As sample bands are detected by the optical fiber, they elute off of the column and remain in the minimized collection volume where they may be collected at any time by a syringe port, sampling pump, or gravity drip. After collection, the collection reservoir is replenished by sample-free buffer and electrophoresis continues. The quantitative trace, electrochromatogram, or electropherogram provided by the optical fiber can be used to trigger fraction collection. Finally, another embodiment employs a CCD or similar, array type device for simultaneous monitoring of the entire column 22 while still using the end-column fluorescence or other optical detection methods to trigger collection.

Operation of the Invention

In operation, any nucleic-acid binding fluorophore which co-migrates with the nucleic acid, or any labeling method which renders the sample fluorescent can be used to detect the molecules of interest just prior to migration off of the gel matrix. Dye molecules can be pre-incubated with the sample mixture prior to electrophoresis or the entire gel may be cast with a dye which undergoes fluorescence enhancement upon binding to the molecules in the sample mixture. Similarly, the gel may have an immobilized fluorophore that interacts with nucleic acid molecules as they migrate past the detection region. Fluorescence Resonance Energy Transfer (FRET) may also be used as a reporting mechanism. In this manner, the electrophoresis apparatus is run in a mode more similar to column chromatography than typical slab-gel electrophoresis. In the preferred embodiment, all nucleic acid molecules, fluorescently labeled proteins run the entire length of the column. Fluorescence detection instead of UV absorbance allows the measurement to be made on-column, obviating the problem of band-broadening, dilution, or dispersion in an off-column detection cell.

Advantages of the Invention

The present invention allows for a simplified method and apparatus for preparative electrophoresis in which any charged biological molecules (especially DNA or RNA), protein, whole cell, organelle, viral particle, nanoparticle, or nano- or microbead being purified is directly eluted into free solution immediately following its detection by an "on-column" optical fiber inserted into or immediately juxtaposed to the separation matrix, for direct precipitation.

The present invention uses an ion exchange membrane to create a small collection volume at the exit of the column. The membrane maintains ionic conductivity, thereby allowing electrophoresis to proceed, while creating a small collection volume that is separate from the remainder of the reservoir buffer. In this manner, the collection volume is effectively minimized without complications of buffer loss to electrolysis, bubble formation, and change in pH. A similar membrane may also be used at the entrance of the column to create a small loading or injection volume.

The use of electrophoresis versus liquid chromatography (FPLC) for preparations of microgram to milligram quantities of DNA or RNA has several advantages. These advantages include a higher number of theoretical plates (more efficient separation), cheaper equipment, faster setup time, and more reproducibility.

In addition to end-column monitoring with an optical fiber, the entire integrated system includes several other advantages over systems described for column electrochromatography on a preparative scale. Elution of the sample into a small volume allows for easy precipitation of the nucleic acid or proteins or other sample treatments that are generally benefited by smaller volumes. The collection compartment can also be filled with a sorbent material specific for the species of interest or for the purposes of further reducing the volume. The sorbent material can be charged beads, particles, silica gel, magnetic beads, ion exchange beads or resins, or biofunctionalized beads for recognizing a target molecule or for catalyzing a chemical transformation that adds in reporting the presence of the analyte.

The present invention leverages the predictable nature and higher separation efficiency of electrophoresis, while eliminating the need for gel extraction techniques and reagents, and also eliminating the time consuming methods used in liquid chromatography.

We claim:

1. A method for separating and preparing biological material comprising:
   incubating a mixture containing biological material with at least one reporting molecule;
   separating said mixture on a chromatographic matrix under an applied driving force;
   detecting at least one biological material of interest in said chromatographic matrix with an optical detector;
   collecting said biological material of interest from a compartment created by a permselective or ion-exchange membrane; and
   passively controlling the pH of said compartment with a large volume of non-circulating anolyte buffer separated from said compartment by said membrane, wherein said compartment is of a much smaller volume than said large volume of anolyte buffer.

2. The method of claim 1, wherein said optical daector detects radiation.

3. The method of claim 1, wherein said optical detector detects at least one biological material through a connection to said chromatographic matrix with at least one optical fiber.

4. The method of claim 1, wherein said biological material is selected from the group consisting of biological molecules, whole cells, viral particles, nanoparticles, organelles, antibodies, antibody-antigen complexes, and any conjugates thereof.

5. The method of claim 1, wherein said separating comprises applying an electric field to said chromatographic matrix.

6. The method of claim 5, wherein said chromatographic matrix is selected from the group consisting of an electrophoresis matrix, a chromatographic monolith, a plurality of stacking gels, a particle bed, an anion exchange medium, an affinity matrix and combinations thereof.

7. A method for separating and preparing biological material comprising:
   incubating a mixture containing biological material with at least one reporting molecule;
   separating said mixture through an electrophoresis medium under an applied electric field between a catholyte chamber and an anolyte chamber;
   detecting at least one biological material of interest in said electrophoresis medium with an optical detector,
   and collecting said biological material of interest from a compartment separated from said anolyte chamber by a permselective or ion-exchange membrane that permits passive control of pH, wherein said anolyte chamber contains a significantly larger volume of a non-circulating compared to the volume of said compartment in order to buffer said compartment.

8. The method of claim 7, wherein said optical detector detects radiation.

9. The method of claim 7, wherein said optical detector detects at least one biological material through a connection to said electrophoresis matrix with at least one optical fiber.

10. The method of claim 7, wherein said biological material is selected from the group consisting of biological molecules, whole cells, viral particles, nanoparticles, organelles, antibodies, antibody-antigen complexes, and any coal agates thereof.

11. The method of claim 7, wherein sad reporting molecule comprises a fluorescence label.

12. The method of claim 11, wherein said detecting comprises synchronously detecting a modulated fluorescence from said fluorescence label.

13. The method of claim 7, further comprising controlling the temperature of said compartment.

14. A method for separating and preparing biological materials comprising:
   incubating a mixture containing biological materials with at least one reporting molecule;
   separating said mixture on a chromatographic matrix under an applied driving force;
   detecting a plurality of biological materials of interest in said chromatographic matrix with an optical detector;
   collecting said plurality of biological materials of interest in a plurality of compartments created by a plurality of permselective or ion-exchange membranes; and
   controlling the pH of each a said compartments with a large volume of anolyte buffer separated train each of said compartments by said membranes, wherein each of said compartments is of a much smaller volume than said large volume of anolyte buffer.

15. The method of claim 14, wherein said optical detector detects radiation.

16. The method of claim 14, wherein said biological materials we selected from the crimp consisting of biological molecules, whole cells, viral particles, nanoparticles, organelles, antibodies, antibody-antigen complexes, and any conjugates thereof.

17. The method of claim 14, wherein said separating comprises applying an electric field to said chromatographic matrix.

18. The method of claim 14, wherein said chromatographic matrix is selected from the group consisting of an electrophoresis matrix, a chromatographic monolith, a plurality of stacking gels, a particle bed, an anion exchange medium, an affinity matrix and combinations thereof.

19. The method of claim 14, wherein said optical detector detects said plurality of biological materials through a connection to said chromatographic matrix with at least one optical fiber.

* * * * *